United States Patent [19]

Metalis et al.

[11] Patent Number: 5,798,695
[45] Date of Patent: Aug. 25, 1998

[54] IMPAIRED OPERATOR DETECTION AND WARNING SYSTEM EMPLOYING ANALYSIS OF OPERATOR CONTROL ACTIONS

[75] Inventors: Sam Anthony Metalis, Long Beach; Samuel Lee Rodriquez, Costa Mesa, both of Calif.

[73] Assignee: Northrop Grumman Corporation, Los Angeles, Calif.

[21] Appl. No.: 832,397

[22] Filed: Apr. 2, 1997

[51] Int. Cl.$^6$ .................................. G08B 21/00
[52] U.S. Cl. .................. 340/576; 340/439; 340/669
[58] Field of Search .................... 340/576, 439, 340/573, 540, 669

[56] References Cited

U.S. PATENT DOCUMENTS

| | | | |
|---|---|---|---|
| 4,104,621 | 8/1978 | Yanagishima et al. | 340/576 |
| 4,450,438 | 5/1984 | Seko et al. | 310/576 |
| 4,463,347 | 7/1984 | Seko et al. | 340/576 |
| 4,496,938 | 1/1985 | Seko et al. | 340/576 |
| 4,581,607 | 4/1986 | Seko et al. | 340/576 |
| 4,586,032 | 4/1986 | Seko et al. | 340/576 |
| 4,594,583 | 6/1986 | Seko et al. | 340/576 |
| 4,611,199 | 9/1986 | Seko et al. | 340/576 |
| 5,057,834 | 10/1991 | Nordstrom | 340/576 |
| 5,465,079 | 11/1995 | Bouchard et al. | 340/576 |
| 5,488,353 | 1/1996 | Kawakami et al. | 340/576 |
| 5,499,182 | 3/1996 | Ousborne | 340/439 |
| 5,570,087 | 10/1996 | Lemelson | 340/576 |

Primary Examiner—Glen Swann
Attorney, Agent, or Firm—Terry J. Anderson; Karl J. Hoch, Jr.

[57] ABSTRACT

An impaired operator detection system for detecting impairment of an operator of any equipment, system, or vehicle which requires continuous compensatory tracking, or nulling, of course deviation error. Operator control actions are characterized as a complex sine wave and then a power spectrum array (PSA) analysis is used to characterize this control action data. Statistical techniques are used to predict the level of operator alertness by comparing the analysis results of the operator's recent control actions to empirical power spectrum array (PSA) analysis data indicative of an unimpaired operator.

14 Claims, 3 Drawing Sheets

IMPAIRED OPERATOR DETECTION AND WARNING SYSTEM EMPLOYING ANALYSIS OF OPERATOR CONTROL ACTIONS

BACKGROUND OF THE INVENTION

1. Technical Field

This invention relates to an impaired operator detection system, a means for detecting impairment in vehicle operators. More particularly, this invention relates to characterizing operator control functions as a complex of sine waves of various frequencies and amplitudes, and then using power spectrum array (PSA) analysis of appropriate periods of control action data to predict the level of the operator's alertness, defined by vehicle control effectiveness, virtually in real-time.

2. Background Art

Whenever a person is responsible for operating a vehicle, it is critical that the person be capable of demonstrating basic cognitive and motor skills that will assure the safe operation of the vehicle. Lack of sleep, boredom or consumption of drugs or alcohol can impair a vehicle operator's ability to safely operate the vehicle. Therefore, it is important when designing an impaired operator detection system to continuously evaluate an operator's ability to control the vehicle.

Impaired operator detection systems are useful because they avoid or reduce personal injury and property damage by preventing accidents. Additionally, such systems may also be useful in documenting the driving record of the driver. If a driver has objective evidence of a good driving record, this person should be eligible for reduced insurance rates. Also, in the case of commercial/fleet vehicle operations, use of evidence from such an impaired operator detection system by employers should reduce their insurance rates as well as their risk of liability for any accidents that may occur as a result of actions of their employees. In addition, this data could also be used to show that a driver is fit for special driving assignments such as ferrying dangerous cargo.

Heretofore, various kinds of drunk or impaired operator detection systems have been used. A number of pre-trip devices, employed both as mockups of actual vehicle controls and installed within a vehicle itself, have been developed which allow a driver's fitness to operate a motor vehicle to be evaluated before the driver begins to operate the vehicle. The problem with such pre-trip devices is that the driver's competence to drive is only measured at the outset of the trip. Degraded driving ability due to fatigue or other events which may impair mental functioning over prolonged driving periods is not taken into account. This is a serious disadvantage with these types of systems, since, understandably, degraded operator vehicle control often occurs over time. In addition, many pre-trip tests are not actually tests of fitness for driving but are tests of level of driver vigilance, balance, perceptiveness, alcohol consumption, etc., which are only tangentially related to the task of driving, and provide no real-time measure of the capability in question.

Another means by which driving ability is measured is by recording operational information regarding drivers and vehicles during vehicle operation. A number of electronic devices exist which record data on various aspects of vehicle performance and/or environment. Such devices have employed magnetic tape and paper strips to record such information. These devices function primarily as trip recorders, storing information such as trip distance, trip time, miles per gallon consumed and average speed. Although they have many uses, these devices cannot detect the impairment of driver control while the vehicle is being operated, only after the fact. In the absence of a real-time assessment capability, these devices cannot serve the function of an impaired driver detector.

Alternately, there are some impaired operator detection systems that operate while the vehicle is being driven. There are a number of known vehicle-borne radar systems which monitor the relationship of a vehicle to other vehicles and obstacles. For example, systems are known that transmit and receive at three different frequencies on a time division basis, with two frequencies being used to determine the range, and the third being combined with one of the first two to determine closing speed and the likelihood of collision. However, such systems are sensitive to temperature changes, difficult to calibrate, limited in resolution and reliability, and require complex processing. Furthermore, such systems are dedicated to particular tasks, such as determining the range and relative rate of motion of other objects, and therefore are difficult to upgrade and customize to meet varying requirements. Additionally, in vehicular radar systems, only a small part of the reflected signal is returned to the antenna. Without sophisticated information processing, it may be difficult to identify and interpret the reflected signal. Such sophisticated signal processing generally requires expensive and complex equipment and algorithms.

Another approach to the real-time monitoring of driver impairment involves taking physiological measures, which are known to vary as a function of level of operator vigilance. When brain waves characteristic of operator drowsiness are detected, the system can trigger appropriate alarms. But the challenges of obtaining an artifact-free brain wave record in real-world settings are daunting. The application of scalp electrodes requires considerable preparation and expertise. The amplification, filtering, and measurement of the brain waves requires very expensive, sophisticated electronic equipment and considerable artistry in the determination of just what brain wave patterns constitute a dangerous level of operator drowsiness, as opposed to full alertness or complete, deep sleep.

Still another approach to the real-time monitoring of driver impairment involves placing a simple mercury switch on the head of the driver, usually attached to eye glass frames. When the driver's head is in the normal position the switch remains open, but when the driver falls asleep the head rolls forward, with the chin coming to rest on the chest. This change in switch position causes the switch to close and an alarm to sound. However, by the time most drivers are in such a deep sleep they will have been below the level of awareness needed to control a vehicle for several seconds, far too late to avoid an accident. And if the sleeping driver's head rolls backward onto the head rest, and so leaves the mercury switch open, the alarm will never sound.

One recurring problem affecting impaired operator detection systems is that of validity, or sensitivity—detecting impairment when it indeed is the case, and not detecting impairment when it is not the case. False alarms, false indications that a driver is impaired, will severely degrade the utility of an impaired driving system. Misses, failures to indicate that an impaired driver is indeed impaired, will also degrade the utility of the system. For example, the system must be able to discern the normal control actions of a competent driver making a lane change or a turn from the abnormal control actions of an impaired driver weaving across the roadway, and must never mistake one for the other.

To prevent the common problems and disadvantages with the prior art's impaired operator detection systems, an improved impaired operator detection system is required. This improved impaired operator detection system should be easy and cost effective to retrofit and customize to existing vehicles, and it should be able to measure vehicle operator competence virtually in real-time in order to warn of the operator's impairedness in time to prevent accidents. This improved impaired operator detection system should also be able to filter out normal driving operations from erratic or impaired driving actions. Such an improved system would provide major advancements in functionality and practicality over the present technology.

Wherefore, in addition to circumventing problems of the prior art, the objectives of the proposed system are to be (1) relatively simple, rugged, and inexpensive to produce, (2) easy to retrofit and customize to existing vehicles, and (3) able to accurately, validly discriminate between normal driving and impaired driving behavior, and reliably do so in a wide variety of real-world driving situations.

SUMMARY

The foregoing objects have been achieved by a system which essentially characterizes operator control actions and/ or the resulting lateral vehicle movements as a complex sinusoidal function and then, using power spectrum array (PSA) analysis of appropriate periods of the data as well as statistical techniques, predicts the level of operator alertness effectively in real-time.

An alert vehicle operator (auto or truck driver, aircraft pilot or the like) will perform small control actions, or inputs to keep the vehicle on track and will focus on the "compensatory tracking" task (i.e., the on-going nulling of any perceived errors between the vehicle's actual path and the desired path). If the operator's mental functioning is diminished for any reason (e.g., as a result of drowsiness), the operator will allow a longer period of time to elapse between successive tracking control actions, so the course error will be greater, necessitating larger and more sudden control actions to null the error. In the case of an auto or truck, an alert driver effectively keeps the vehicle in the middle of its lane, whereas the impaired driver allows it to display considerable side-to-side, or lateral, course deviation errors. If these lateral course deviations or their correlates (e.g., steering wheel actions) are plotted they resemble a complex sine wave of constantly changing frequency and amplitude. Such changes in the energy of a complex sine wave over a block of time, or an epoch, can be accurately characterized through the use of PSA analysis, a well known mathematical technique. Thus, a PSA analysis of appropriate epochs of control action data can be used to predict the level operator alertness.

The impaired operator detection system of the present invention includes a sensor that provides a measurement of the operator's vehicle control actions and generates a signal which approximates a sine wave of varying frequency and amplitude. It also includes an analyzer which processes the signal received from the sensor by converting it into the frequency domain using a Fast Fourier Transform (FFT) algorithm. A numeric description of wave frequency and amplitude is then obtained using the PSA. The measured data is then compared against "alert driver" data. If the comparison shows that the PSA of the measured data is unlikely to be from that of an unimpaired operator, then a warning is issued or contingencies are put into effect.

Steering wheel corrections can easily be sensed by using an accelerometer. Such accelerometers are small, simple, commercially available and reliable. Thus, retrofitting present vehicles is easy and commercially viable. Additionally, software to perform the numerical functions of this invention, such as the FFT and statistical comparison, is readily available. Thus, the high cost, and problems in accuracy, complexity and reliability of the prior art are also avoided. Since the impaired operator detection of the present system functions continuously and virtually in real-time the disadvantages of the pre-trip impaired operator detection systems are also avoided. Additionally, the system of the present invention utilizes an analysis method which allows it to reduce the miss and false alarm rates, and thereby increases effectiveness.

In addition to the just described benefits, other objectives and advantages of the present invention will become apparent from the detailed description which follows hereinafter when taken in conjunction with the drawing figures which accompany it.

DESCRIPTION OF THE DRAWINGS

The specific features, aspects, and advantages of the present invention will become better understood with regard to the following description, appended claims, and accompanying drawings where:

DETAILED DESCRIPTION OF THE PREFERRED EMBODIMENTS

Figure 1:
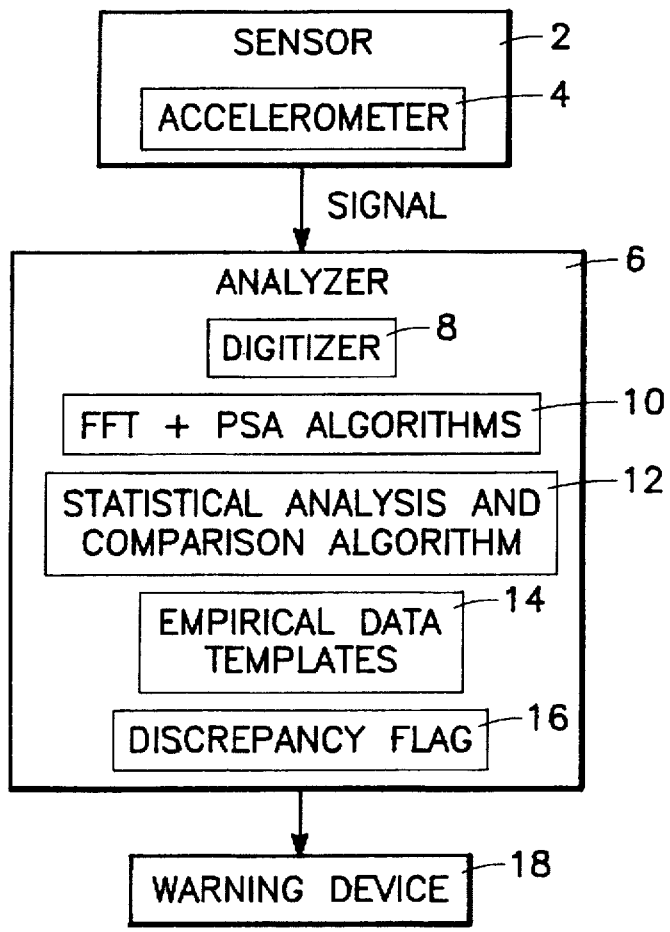
FIG. 1 is a schematic of the impaired operator detection system of the present invention.

In the following description of the preferred embodiments of the present invention, reference is made to the accompanying drawings which form a part hereof, and in which is shown by way of illustration specific embodiments in which the invention may be practiced. It is understood that other embodiments may be utilized and structural changes may be made without departing from the scope of the present invention.

The impaired operator detection system of a preferred embodiment of this invention uses a vehicle's lateral acceleration, jitter, or at least the portion due to the nature of the driver's control inputs, to predict the point on the alertness continuum at which the driver is operating. More importantly, this invention can be used to accurately and reliably detect when the operator is not in the safe range of the alertness continuum.

Other factors being equal, an alert driver will drive down the road with greater accuracy in lane tracking than will a drowsy or otherwise mentally impaired driver. The driver's task is to observe the vehicle's path relative to the roadway, detect any deviations from the path, determine the steering wheel correction required to correct the deviation, and make the required correction. In other words, the driver performs a three-phase mental process of perception, evaluation and reaction. A driver in full possession of their mental faculties will perform this three-phase mental process quickly and accurately. Thus, deviations from the path will be corrected quickly, before they can become very large. The driver will be constantly making small, measured corrective adjustments to the steering wheel, so small as to seem imperceptible. An accelerometer mounted on the alert driver's vehicle will sense few, if any, sudden lateral accelerations. By definition, this is good driving. Poor driving, on the other hand, happens when a driver does not perform the three-phase mental process well. As a result, deviations from the path will be perceived and corrected only when they become relatively large. The driver's steering wheel activity will consist of occasionally making sudden, large corrective adjustments to compensate for the large path deviation error that has accumulated since the last adjustment. The adjustments will be sporadic, interspersed with periods when almost no adjustments are being made. An accelerometer mounted on the impaired driver's vehicle will sense frequent, large, sudden lateral accelerations.

The impaired operator detection system of the present invention operates by measuring any measure of jitter due to the operator's control actions while driving which may be characterized as a complex sine wave. In the preferred embodiment, the lateral velocity changes, lateral accelerations, or jitter, that accompanies the forward movement of the vehicle is characterized as a series of sine waves of varying frequencies and amplitudes occurring over a fixed period of time, or epoch. A numeric description of wave frequency and amplitude is obtained using a power spectrum array (PSA) analysis. The algorithms required to compute the PSA are known and can be implemented in a number of ways in virtually real time. However, other techniques for obtaining a numeric description of the waveforms characteristic of impaired operator control may also be employed (e.g., characteristic templates based on wavelet analysis).

In the preferred embodiment, the energy due to the control actions of the operator is grouped into each of several frequency bands, selected so as to highlight the most informative bands in the PSA. A portion of the jitter will be due to road conditions, a portion will be due to coarse changes in vehicle direction, such as changing lanes, and a portion will be due to the fine changes involved in just keeping the vehicle going in the desired direction. The lateral velocity changes of the alert driver, the one who is making many fine, timely course corrections, will be characterized by relatively little energy, and what energy there is will be in relatively low frequency bands. The lateral accelerations of the impaired driver, the one who is making sporadic, large and sudden course corrections, will be characterized by relatively high energy, and the energy will be in relatively higher frequency bands.

An item of practical import to the present invention is the epoch duration of each PSA sample. An epoch that is too brief may not permit the capture of enough data to characterize that portion of the lateral acceleration data due to the operator alertness factors, and one that is too long may result in data due to extraneous factors masking the portion due to alertness factors. Furthermore, the sample frequency is important because if the discrepancy flag can be set only occasionally, at the end of a long duration epoch, then the warning concerning a dangerous decrease in alertness will come too late to be of benefit. An effective method of dealing with these issues is through a so-called "cascade" analysis approach. A determination is initially made as to how often the alertness level must be assessed in order to provide timely feedback should a warning alarm need to be sounded. This becomes the sampling frequency or warning window. A second determination is made concerning the epoch size needed to capture characteristic PSA signatures, the sampling epoch. The sampling epoch in the preferred embodiment of this invention is on the order of 30 seconds. It is believed that a 30 second epoch will allow the data to be characterized properly, but will not be so short as to be significantly effected by normal driving maneuvers, such as a turn for obstacle avoidance, or so long as to obscure the portion of the control activities due to operator alertness with those activities due to extraneous factors. The warning window in the preferred embodiment is about five seconds so that, in virtually real-time, impaired driving is identified and the driver is warned before loss of control of the vehicle occurs. The ratio of sampling epoch time to warning window time determines how many cascaded, or concurrent PSA analyses must be performed by the system. With a 30 second sampling epoch and five second warning window, six analyses would need to be performed concurrently. If, instead, a more conservative two second warning window were selected, and the 30 second sampling epoch were unchanged, then 15 analyses would need to be performed concurrently. The value of this improvement in warning window resolution would need to be weighed against the increase in cost of the system hardware needed to perform the concurrent analyses, as well as the quickness of changes in operator alertness that the system is required to detect. For example, if, instead of monitoring the slow change from alertness to drowsiness in a highway vehicle driver, the system were to monitor the rapid transition from alertness to unconsciousness in a high performance aircraft pilot succumbing to gravity-induced loss of consciousness, then the impaired operator detection system might best be set to a ten second sampling epoch and a one second warning window.

A preferred embodiment of the present invention uses a PSA analysis procedure to characterize the vehicle's lateral acceleration. For a given sampling epoch, the energy or power characterizing lateral acceleration of the vehicle and present in each of several candidate frequency bands (e.g. 4 bands: 0.0–0.3 Hz; 0.30–0.6 Hz; 0.6–0.9 Hz; 0.9–1.2 Hz) is computed. Given a sampling epoch of 30 seconds and a warning window of 5 seconds, then every five seconds a new analysis of the preceding 30 seconds of data is initiated. The band between 0.0 and 0.3 Hz describes the course changes elicited by external factors, such as the contours of the road, lane changes, and so forth. The bands between 0.3 to 0.6 Hz and 0.6 to 0.9 Hz are most predictive of driver alertness. The alert driver will exhibit much less energy than the drowsy driver within the bands, and the energy is more likely to be concentrated in the lower of the two frequency bands. The band between 0.9 to 1.2 Hz typically has little energy, but what there is may be in part caused by sudden, jerky corrections of the drowsy or impaired driver.

The measured data is thus compared against the "alert driver" pattern distribution and then, using inferential statistics, the likelihood that it is a member of that distribution is computed. Hence, the present invention includes a template matching algorithm. Templates or patterns are constructed from a statistical distribution of those sampling epoch PSAs that characterize the lateral velocity changes of the vehicle obtained during normal driving conditions with an alert driver in control. These templates are matched against the PSA of the current sampling epoch. Inferential statistics are used to specify the degree to which the current sampling epoch is likely to be a member of the template distribution of alert driver sampling epochs. If the analysis indicates it is unlikely to be a member of the distribution, then a discrepancy flag is set, indicating that the driver's alertness must be questioned. This analysis looks at the past 30 seconds of data but does so every five seconds, thereby yielding the current status of driver alertness frequently so that no more than about five seconds of "non-warned" driving occurs between opportunities to warn. Hence, the invention operates to warn the operator virtually in real time. An alarm may be sounded to inform the driver that he is not driving well.

A preferred embodiment of an impaired operator detection system in accordance with the present invention is shown in FIG. 1. In this preferred embodiment of this invention, a sensor device 2 which includes an accelerometer 4 is used to measure the lateral displacement of the vehicle while the vehicle is being driven. This data, in the form of a complex sinusoidal signal, is provided to an analyzer 6, which in this preferred embodiment is a microprocessor. The data is digitized within a digitizer 8 resident in the analyzer 6. A numeric description of wave frequency and amplitude for a given sampling epoch is obtained using a power spectrum array (PSA) derived from the Fast Fourier Transform (FFT) algorithm 10 on the digitized data. Statistics are used to test the hypothesis that the current sampling epoch is a member of the template distribution of alert driver sampling epochs. A statistical analysis and comparison algorithm 12 is then used to compare the measured data in the frequency domain to comparable empirical data templates 14 which characterize an alert driver. These data templates are stored in the processor memory. These templates 14 are constructed from a statistical distribution of the sampling epoch PSAs that characterize the lateral velocity changes of the vehicle obtained during normal driving conditions with an unimpaired driver. If the analysis indicates that the PSA of the current sampling epoch is unlikely to be a member of the distribution, then a discrepancy flag 16 is set, indicating that the driver's alertness must be questioned and other contingencies take effect. A warning alarm device 18 may be sounded to inform the driver that he is not driving well. In the case of an aircraft with an unconscious pilot, the contingency may involve an automatic, pre-programmed recovery maneuver by the autopilot.

Figure 2:
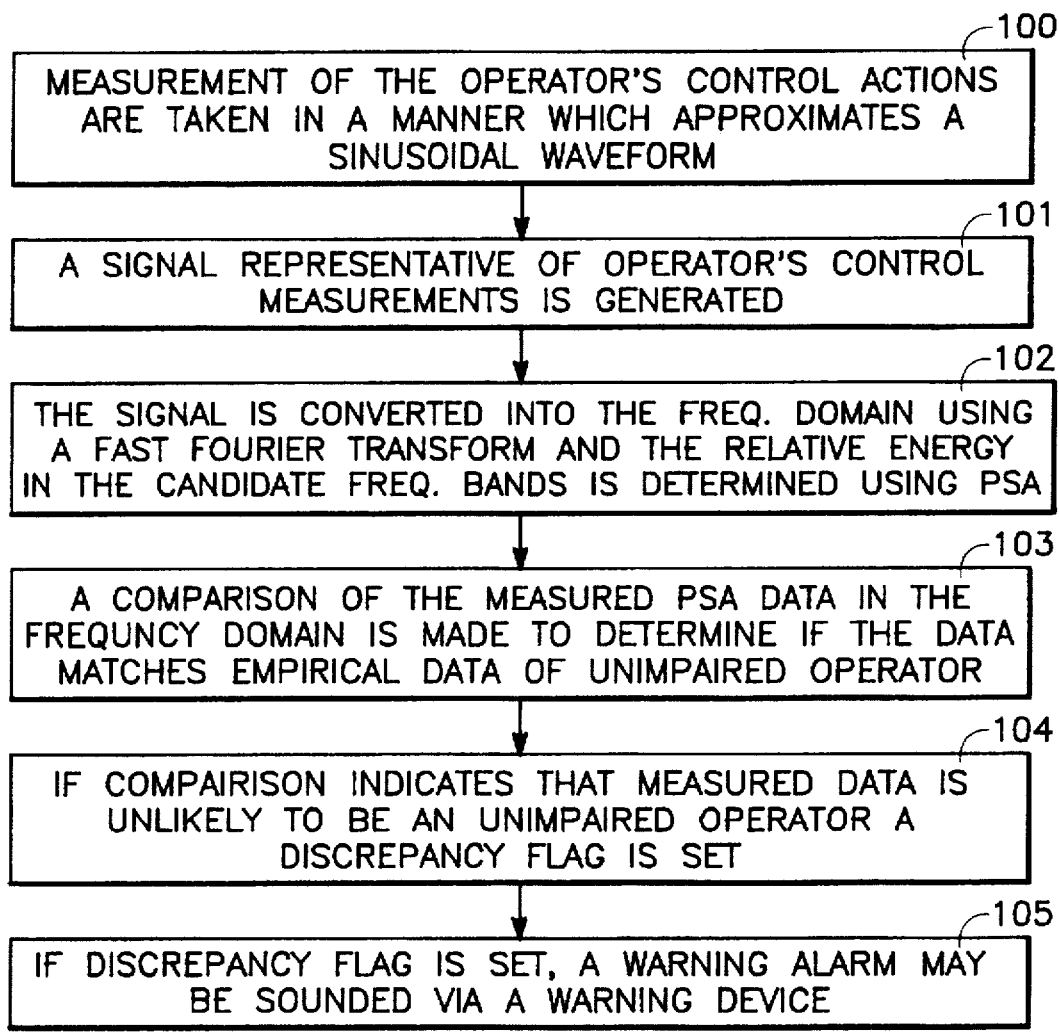
FIG. 2 is a flow chart of the impaired operator detection system of the present invention.

FIG. 2 describes a preferred process employable with the above-described impaired operator detection system. In step 100 measurements of the operator's course correction actions are taken. Examples of such data include data from sources such as steering wheel inputs, the angular relationship of the front wheels relative to the forward movement of the vehicle on the road or, as in the preferred case, data from an adequately sensitive accelerometer. A signal representative of the control measurements is generated in step 101. In step 102, the signal is converted into the frequency domain using a Fast Fourier Transform. A numeric description of wave frequency and amplitude of the current sampling epoch is then obtained using a power spectrum array (PSA) derived from the Fast Fourier Transform (FFT) algorithm. In Step 103, inferential statistics are used to determine whether or not the current sampling epoch PSA is likely to be a member of an alert driver distribution. If the analysis indicates that the PSA of the current epoch is unlikely to be a member of the distribution, then a discrepancy flag is set in step 104, indicating that "impaired operator" contingencies must be put into effect (e.g., sounding the warning alarm device 105).

Figure 3:
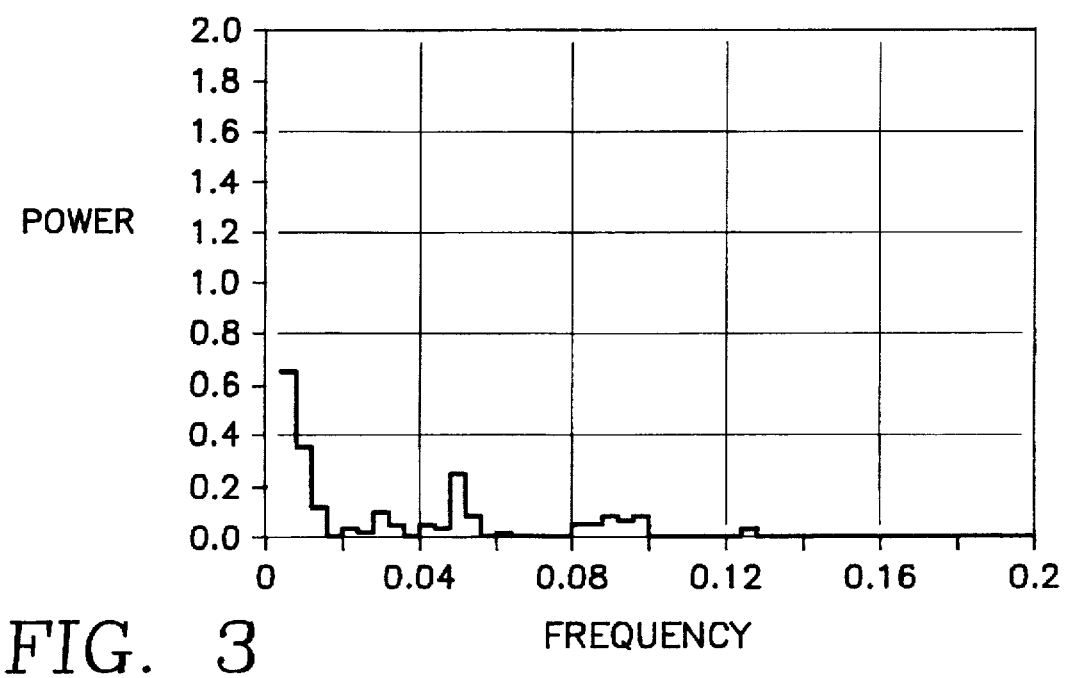
FIG. 3 is a power spectrum plot of an alert driver (Subject 1).
Figure 4:
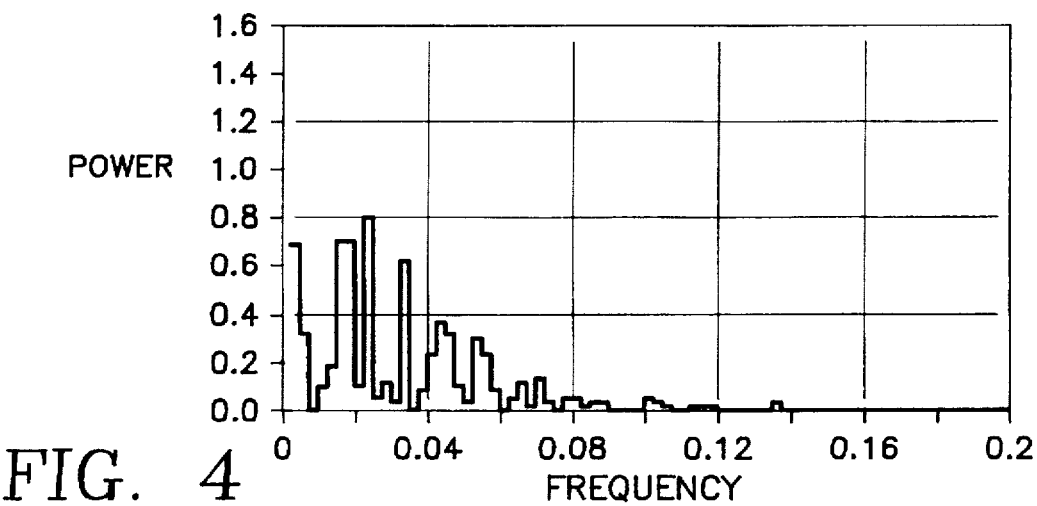
FIG. 4 is a power spectrum plot of a drowsy driver (Subject 1).
Figure 5:
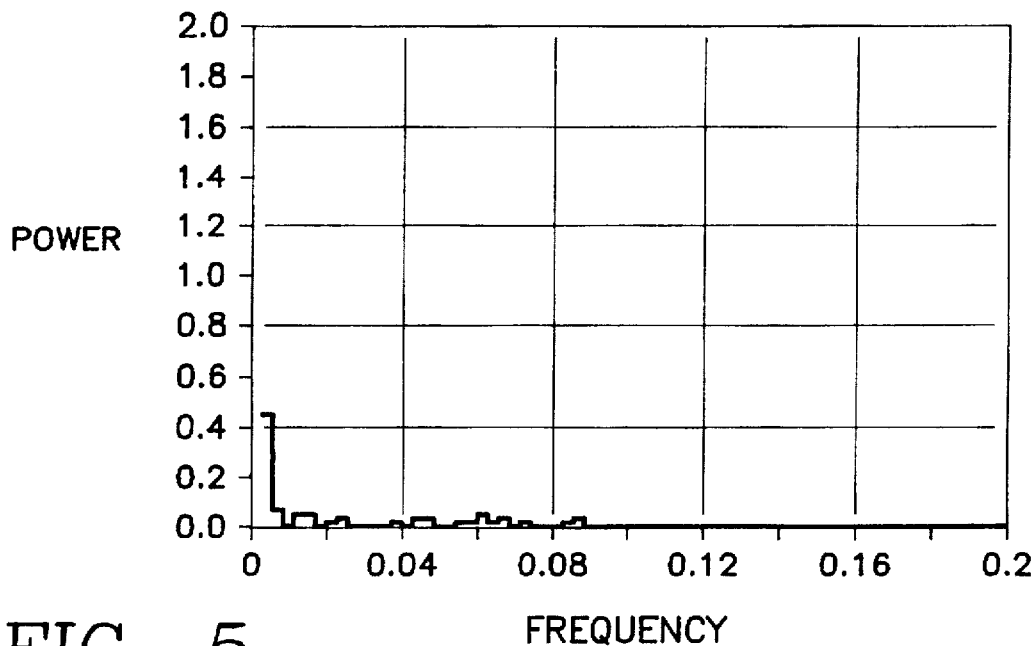
FIG. 5 is a power spectrum plot of an alert driver (Subject 2).
Figure 6:
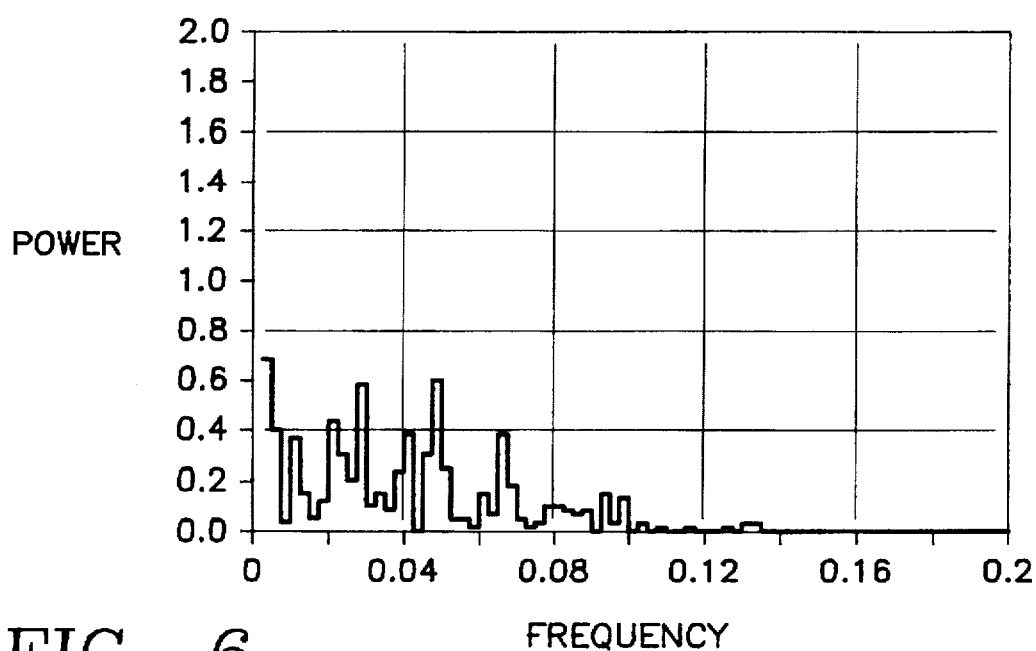
FIG. 6 is a power spectrum plot of a drowsy driver (Subject 2).

This invention has been tested in a rough prototype configuration. An experiment was conducted wherein each of two subjects drove a simulated car for several hours at a fixed speed around an egg-shaped track. This necessitated that the driver make small but constant steering wheel corrections throughout the duration of the test trial. The vehicle was placed in automatic cruise control, so that the apparent speed was a constant 40 miles per hour. By simplifying the task so that the driver never needed to use the brake or gas pedals, the driving task was rendered more boring. On one occasion the subject drove while alert. On another occasion the subject drove while sleep deprived. Each drive around the loop, or trial, took a little more than 17 minutes. Epochs of about four minutes of steering wheel control input data were recorded, along with lane centerline deviation (course error) data, the operational definition of alertness in this study. The centerline deviation data served to independently corroborate the drivers' performance accuracy. This test was repeated for two different subjects. As expected, course error for both subjects was poorer under the sleep deprived condition. Steering wheel control inputs, when analyzed via PSA analysis using a conventional mathematical software package, revealed clear differences in the energy bands that best characterized the two conditions. FIGS. 3 and 4 for Subject 1 and FIGS. 5 and 6 for Subject 2 provide data from alert and drowsy conditions, respectively. Further analyses revealed that sampling epochs of 30 seconds duration were as informative as the four minute epochs, given the particulars of this experiment.

Although the preferred embodiment uses a microprocessor and programming embodying the previously described algorithms to perform analysis, the processing could be done using logic circuitry specifically designed to perform the above processing. Additionally, although the preferred embodiment of the present invention uses an accelerometer to measure lateral displacement of the vehicle, any measured variable that reflects continuous tracking error, or course correction error, in the operator's control of a vehicle and can be generally described as a complex sine wave can be successfully used in the present invention.

While the invention has been described in detail by specific reference to preferred embodiments thereof, it is understood that variations and modifications thereof may be made without departing from the true spirit and scope of the invention. Although the above invention is described relative to the detection of an impaired car or truck vehicle operator, this same invention could be used to detect operator impairment of other machinery. For example, the impaired operator detection system may be employed to assess the mental fitness of a high performance aircraft pilot who may be experiencing G-LOC (gravity induced loss of consciousness). Unconsciousness results from a reduction of blood to the pilot's brain, due to the increase in gravity resulting from a sudden change in aircraft flight path, characteristic of a sudden evasive maneuver. The pattern of stick control activity of a conscious pilot would, of course, be quite different from that of an unconscious pilot, so the invention could easily serve to detect this dangerous, but quite common, state of operator incapacitation.

Wherefore, having thus described the present invention, what is claimed is:

1. An impaired operator detection system comprising:

a sensing device that provides a measurement of the operator's control actions and that generates a signal indicative of said control actions; and an analyzer comprising a processor which includes, a Fast Fourier Transform processor portion capable of performing a Fast Fourier Transform on said signal and converting the transformed signal into a Power Spectrum Array (PSA) comprising a numeric description of the waveform energy present in each of a chosen series of frequency bands, and a comparison processor portion capable of comparing the PSA derived from said measurement of the operator's control actions to at least one empirical PSA created from empirical data indicative of an unimpaired operator.

2. The impaired operator detection system of claim 1 wherein the sensing device generates a signal representative of a prescribed sample period, the sampling epoch, of completed operator control actions and the Fast Fourier Transform processor portion performs the Fast Fourier Transform and conversion of the transformed signal into a PSA on said signal representative of the prescribed sampling epoch, said signal generation and analysis being iteratively repeated at a prescribed offset period referred to as a warning window.

3. The impaired operator detection system of claim 2 wherein said sampling epoch is approximately 30 seconds and said warning window is about five seconds.

4. The impaired operator detection system of claim 1 wherein the analyzer comprises a digitizer processor portion that digitizes said signal produced by said sensing device.

5. The impaired operator detection system of claim 1 further comprising a warning apparatus which is engaged when said PSA derived from said measurement of the operator's control actions has a low probability of matching the at least one empirical PSA created from the empirical data indicative an unimpaired operator.

6. The impaired operator detection system of claim 1 wherein said sensing device comprises an accelerometer.

7. The impaired operator detection system of claim 1 wherein the operator's control actions are characterized by measuring the lateral velocity change of the vehicle.

8. The impaired operator detection system of claim 1 wherein said analyzer is a microprocessor.

9. A method of detecting an impaired operator comprising the steps of:

(a) measuring the operator's control actions;

(b) generating a signal indicative of said control actions;

(c) processing said signal by performing a Fast Fourier Transform on the signal and converting the transformed signal into a Power Spectrum Array (PSA) comprising a numeric description of the waveform energy present in each of a chosen series of frequency bands; and (d) comparing the PSA derived from said measurement of the operator's control actions to at least one empirical PSA created from empirical data indicative of an unimpaired operator.

10. The method of claim 9 further comprising the step of:

(e) warning the operator when said PSA derived from said measurement of the operator's control actions has a low probability of matching the at least one empirical PSA created from the empirical data indicative an unimpaired operator.

11. The method of claim 9 wherein the signal generating step comprises generating a signal representative of a prescribed sampling epoch of completed operator control actions and wherein said processing step comprises performing the Fast Fourier Transform and conversion of the transformed signal into a PSA on said signal representative of the prescribed sampling epoch, said signal generating and characterizing being continuously repeated at a prescribed offset period referred to as a warning window.

12. The method of claim 11 wherein the sample epoch is approximately 30 seconds and said warning window is about five seconds.

13. The method of claim 9 further comprising a step of digitizing said signal indicative of said control actions.

14. The method of claim 9 wherein the measuring step comprises measuring the lateral velocity change of the vehicle.

* * * * *